United States Patent [19]
Hesslewood et al.

[11] Patent Number: 5,827,678
[45] Date of Patent: Oct. 27, 1998

[54] ASSAY REAGENT COMPRISING KILLED BACTERIAL CELLS WHICH RETAIN FUNCTIONAL METABOLIC ACTIVITY

[75] Inventors: Ian Philip Hesslewood, Amersham; Gordon Sydney Anderson Birnie Stewart, Loughborough, both of United Kingdom

[73] Assignee: Merck Patent GmbH, Darmstadt, Germany

[21] Appl. No.: 605,160

[22] PCT Filed: Sep. 5, 1994

[86] PCT No.: PCT/GB94/01926

§ 371 Date: Jul. 17, 1996

§ 102(e) Date: Jul. 17, 1996

[87] PCT Pub. No.: WO95/07346

PCT Pub. Date: Mar. 16, 1995

[30] Foreign Application Priority Data

Sep. 8, 1993 [EP] European Pat. Off. .............. 93307065

[51] Int. Cl.[6] ..................................................... C12Q 1/02
[52] U.S. Cl. .................................. 435/29; 435/4
[58] Field of Search .............................. 435/172.3, 6, 29, 435/4, 975, 172.1; 424/184.1, 201.1

[56] References Cited

U.S. PATENT DOCUMENTS

| | | | |
|---|---|---|---|
| 4,581,135 | 4/1986 | Baldwin | 435/172.3 |
| 4,581,335 | 4/1986 | Baldwin | 435/172.3 |
| 5,486,452 | 1/1996 | Gordon et al. | 435/5 |

FOREIGN PATENT DOCUMENTS

| | | | |
|---|---|---|---|
| 2 005 018 | 4/1979 | United Kingdom . | |
| WO 85/00890 | 2/1985 | WIPO . | |

OTHER PUBLICATIONS

Dox et al (The Harper Collins Illustrated Medical Dictionary, 1993, p. 501).

Mantel et al., "The Effect of Radiation on Bioluminescent Bacteria: Possible Use of Luminescent Bacteria as a Biological dosemeter," Phys. Med. Biology, 1983, 28, 599–602.

Kaplan, "Macromolecular Basis of Radiation–Induced loss of Viability in cells and Viruses," Actions Chimiques ert Biologiques des Radiations: The Chemical and Biological Action of Radiations, Chapt. II, Haissinsky, ed., 1968, 12, 71–94.

Stults et al., "Use of Recombinant Biotinylated Aequorin in Microtiter and Membrane–Based Assays: Purification of Recombinant Apoaequorin from *Escherichia coli*," Biochemistry, 1992, 31, 1433–1442, Jan. 1992.

Journal of Pharmacy and Pharmacology, vol. 18, No. Supp, 1966, London GB, pp. 33S–38S, N.D. Harris and M. Whitefield "The effect of the addition of manganese dioxide to media on the viability of bacteria damaged by x–rays, phenol and radiomimetic agents".

Actions Chimiques Biologiques Et Radiations, vol. 12, 1968, Paris, FR, pp. 71–94, Henry S. Kaplan "Macromolecular basis of radiation–induced loss of viability in cells and viruses".

Physics in Medicine and Biology, vol. 28, No. 5, 1983, London GB, pp. 599–602, J. Mantel et al., "The effect of radiation on bioluminescent bacteria as biological dosemeter".

Mutation Research, vol. 267, No. 1, May 1992, Amsterdam NL, pp. 19–30, C. Seymour et al., "All colonies of CHO–K1 cells surviving gamma–irradiation contain non-viable cells".

*Primary Examiner*—Gary E. Hollinden
*Assistant Examiner*—Dameron Jones
*Attorney, Agent, or Firm*—Wenderoth, Lind & Ponack, L.L.P.

[57] ABSTRACT

The invention is directed to an assay reagent comprising bacteria cells which have been killed but which retain a functional metabolic activity. The assay reagent is useful in a method for assaying an analyte when the functional metabolic activity of the killed cells is signal-generating. A kit for assaying an analyte using the assay reagent of the invention is also provided.

9 Claims, 3 Drawing Sheets

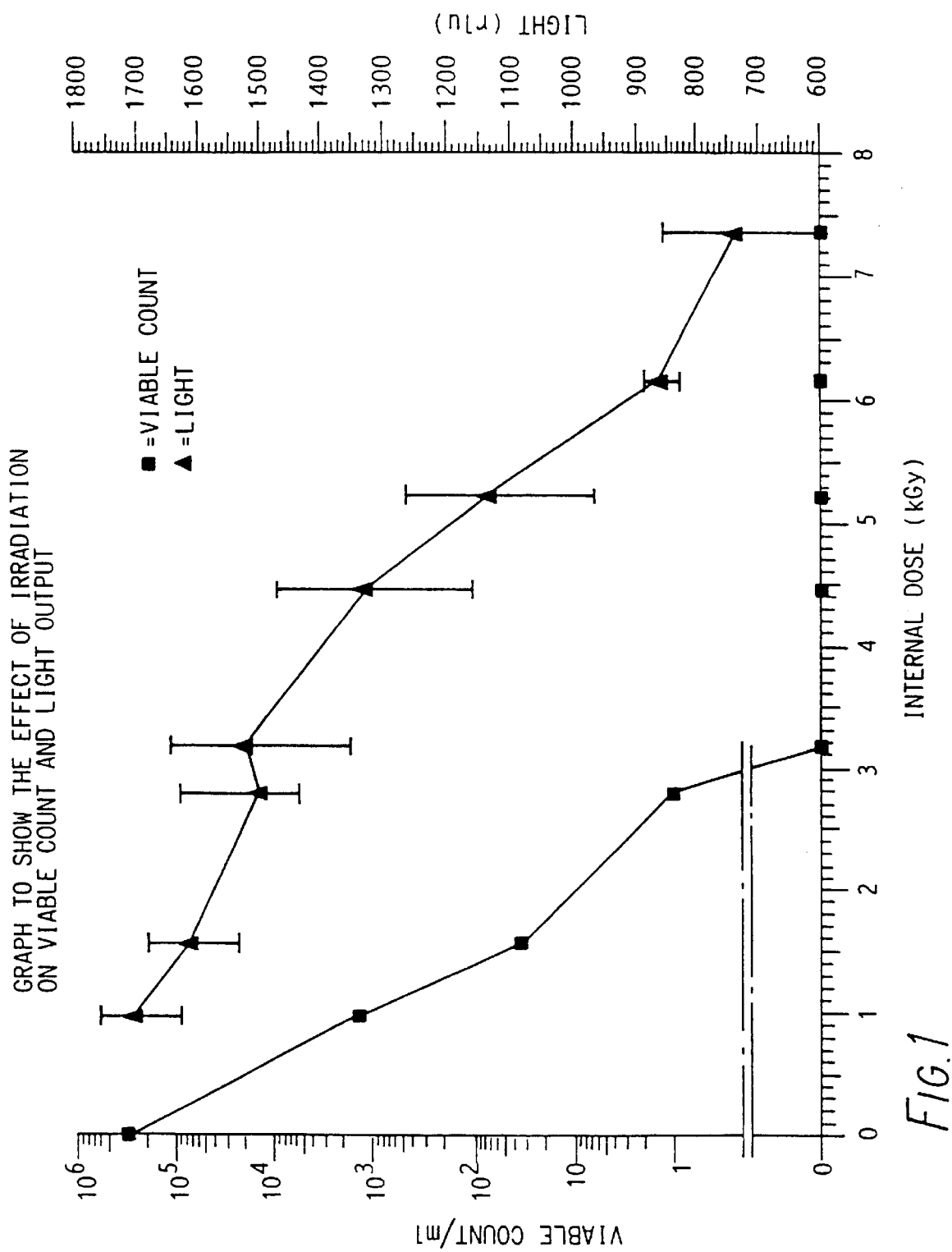

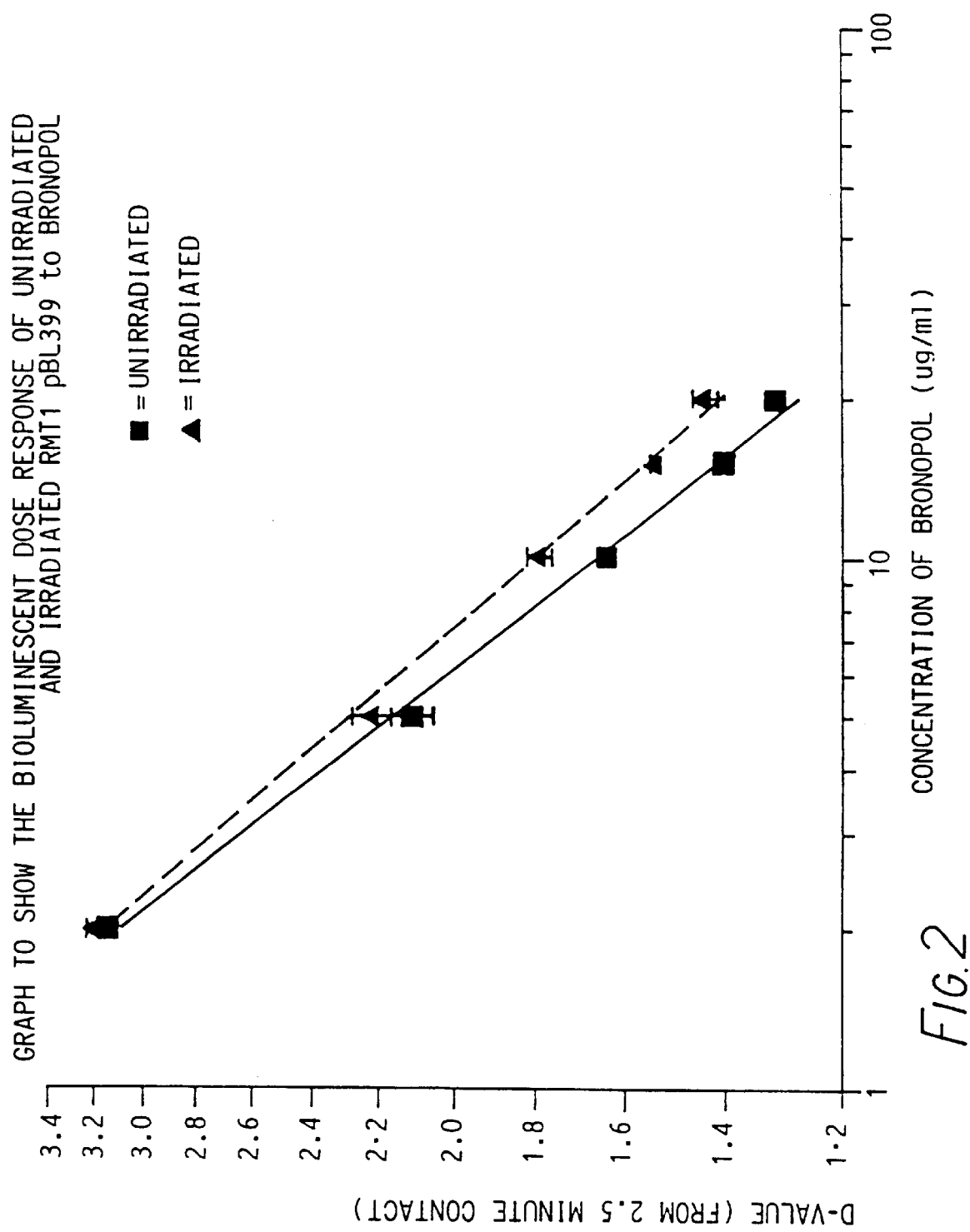

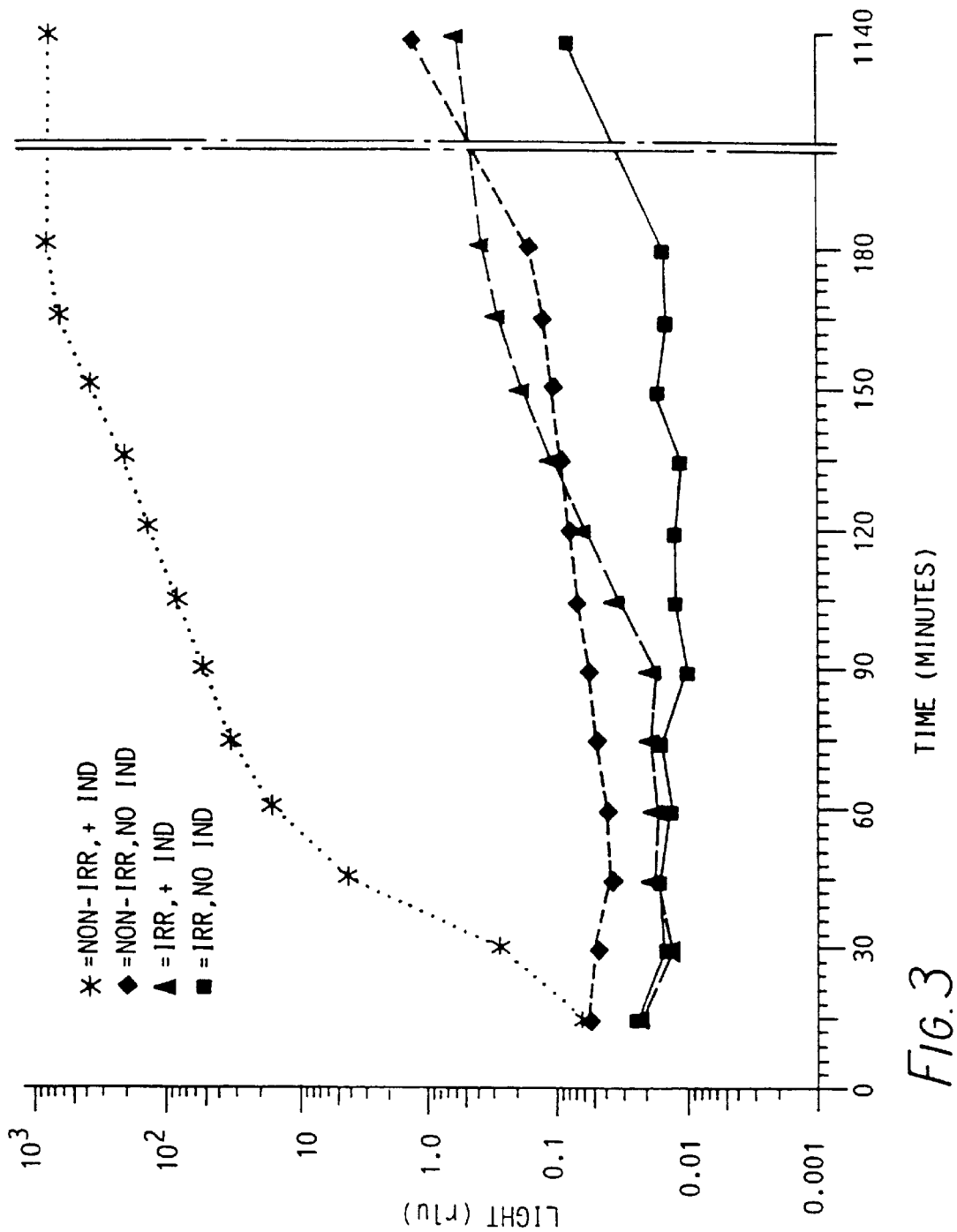

ASSAY REAGENT COMPRISING KILLED BACTERIAL CELLS WHICH RETAIN FUNCTIONAL METABOLIC ACTIVITY

BACKGROUND OF THE INVENTION

1. Field of the Invention

The invention relates to a cell reagent, an assay method for measuring an analyte and a kit therefor.

2. Description of Related Art

British patent specification No. 2,005,018 describes a method of detecting a toxic substance by forming a suspension of a luminous micro-organism in an aqueous medium, contacting the suspension with the toxic substance, and sensing a decrease in the light output of the luminous micro-organisms caused by the toxic substance. An as-say kit embodying this principle is marketed by Microbics Inc. under the Trade Mark Microtox, and is in routine use in a number of environmental laboratories.

Although the Microtox kit is believed to use a naturally occurring bacterium, there is interest in the use of genetically modified luminous micro-organisms, as they potentially have a wider area of application. For example, different micro-organisms can be made with sensitivities to different ranges of toxic substances or even individual toxic substances. The use of genetically modified organisms for this purpose is described in U.S. Pat. No. 4,581,335.

There is an increasing need to perform these assays at the site of potential pollution, and this may well involve tests outside normal laboratory facilities. But such cells are often pathogenic or subject to controlled use. One potential problem when using genetically modified organisms is the possibility that they might escape into the environment and cause harm by growing in an uncontrolled manner. Legal restrictions on use of genetically modified organisms in the field are, or may be, applied in various countries.

It is an object of this invention to avoid the above problem by using genetically modified organisms which have been killed. But as is explained below, the invention is not limited to genetically modified organisms, nor to organisms that emit light, nor to organisms for use in the stated assay for toxic substances.

When micro-organisms are subjected to increasing doses of ionizing radiation, the organisms viability progressively decreases. Thus, a dose of 26 kGy is recommended for sterilizing micro-organisms, and is amply sufficient to reduce their viability to zero.

Non-recombinant luminescent organisms have been subjected to ionising radiation, and the luminescent property used to monitor the radiation dose (Phys. Med. Biol. 28, 599–602, 1983). But the radiation doses were not sufficient to kill all the organisms present.

SUMMARY OF THE INVENTION

In one aspect, this invention provides an assay reagent comprising bacterial cells which have been killed but which retain a functional metabolic activity, the reagent not containing corresponding bacterial cells which have not been killed.

Cells which have been killed have 0% viability. They are unable to reproduce. Cells preferably retain a detectable functional metabolic activity and structural function including one or more of the following properties: cell-wall integrity; membrane/energy function; co-factor provision; metabolic requirement; gene expression; protein synthesis; cytoplasmic enzyme activity; vegetative metabolic processes involving energy usage and transfers.

Preferably the detectable functional metabolic activity is bioluminescence. It will be appreciated that continued bioluminescence may involve continued protein synthesis. It is surprising that cells which have been killed nevertheless retain a functional metabolic activity, such as bioluminescence, albeit at reduced intensity compared to the non-irradiated cells. More surprising is the fact that the functional metabolic activity in these killed cells is altered in a dose-responsive way by substances which alter the functional metabolic activity in a dose-responsive way in the corresponding living cells. Thus, for example, luminescence of killed bioluminescent organisms is changed in a dose-responsive way in the presence of a substance which is a toxicant for the corresponding living organism.

Preferably the cells used in this invention are micro-organisms which may be genetically modified organisms. Often, the micro-organisms are bacteria. *E. coli* bacteria were used in the examples below, but other bacteria could have been used with equivalent effect. The cells may be stored and presented in a stabilised state. Preferably this stabilized state may be lyophilized.

The cells may have been killed by radiation e.g. ionizing radiation. The gamma-radiation from a cobalt-60 source was used in the examples below. But gamma-radiation from other sources, or X-rays, or an electron beam, or even ultraviolet radiation, could have been used with equal effect. The radiation damage must be sufficient to kill the cells, but should preferably be not much greater than is necessary for that purpose. This is because the radiation damage also progressively reduces the bioluminescence or other functional metabolic activity of the organisms. The required radiation dose depends on the number of cells present, e.g. on the cell density, and on the nature of the cells, and is quite easily determined by routine experiment, as demonstrated in the examples below. Killing the cells by other means, without at the same time destroying all their functional metabolic activity(ies), is possible but not preferred.

In another aspect, the invention provides use of the cells, which have been killed but which retain a functional metabolic activity, in a bio-assay. One example of a bio-assay is the assay for toxicant mentioned above.

Thus in another aspect, the invention provides a method of assaying an analyte, by the use of a liquid suspension of signal-generating cells, which comprises mixing together a liquid sample possibly containing the analyte and an aliquot of the liquid suspension to form a test mixture and thereafter observing a signal generated by the cells, wherein the cells have been killed, preferably by ionizing radiation, but retain a signal-generating functional metabolic activity, preferably bioluminescence.

In yet another aspect, the invention provides a kit for performing the stated assay, comprising a supply of bacteria, which bacteria have been killed but retain a signal-generating functional metabolic activity such as bioluminescence; a supply of a reconstitution buffer; means for handling the liquid samples and liquid aliquots, such as containers and pipettes for performing the assay; and optionally also an instrument for measuring the signal. The bacteria are preferably in a stabilised state, e.g. by being lyophilized or frozen.

The nature of the analyte is not material to the invention. Many analytes especially toxicants are well known which have the effect of reducing the bioluminescence or other signal generated by living cells. Toxicants—and the inventors have tested a series—have a corresponding effect, of reducing the bioluminescence or other signal generated by the killed cells of this invention. Other analytes may have the property of inducing de novo gene expression in the killed cells (see Example 3).

BRIEF DESCRIPTION OF THE FIGURES

Reference is directed to the accompanying drawings, in which:

FIG. 1 is a graph to show the effect of irradiation on viable count and light output;

FIG. 2 is a graph to show the effect of irradiation on the sensitivity of the light reagent to Bronopol; and FIG. 3 is a graph to show the effect of irradiation on the induction of bioluminescence in noninduced bioluminescent E. coli.

DETAILED DESCRIPTION OF THE PREFERRED EMBODIMENTS

EXAMPLE 1

Method
1. Each box was packed with 60 vials of LUX light reagent (a lyophilized sample of genetically modified bacteria in which the LUX gene responsible for bioluminescence was present in a plasmid, the suspension having a starting $OD_{630}$ of 0.9 in polypropylene vials), with a dosimeter placed in the center.
2. Boxes were taped securely and subjected to external doses of radiation from a cobalt-60 source in the range of 1–8 kGy.
3. 2 mls of sterile CLPB (controlled log phase broth (Lab M)) was injected aseptically into three vials from each box using a syringe and sterile needle and into 3 vials which had not been irradiated.
4. Duplicate samples were plated onto Luria Agar plates.
5. Plates were incubated overnight at 30° C. before counting. The results are shown in FIG. 1, where the filled squares represent the viability counts.
6. Five vials were reconstituted using 0.5 ml BAR3 buffer (25 mM HEPES pH 6,50 mM NaCl, 12.5 mM $MgSO_4$) and left for 20 minutes at room temperature.
7. The light output was read in a luminometer. The results are shown in FIG. 1, where the filled triangles represent light outputs at different levels of irradiation. As can be seen, an internal radiation dose of 3.5 kGy was enough to kill the cells, but by no means extinguished the light output.

EXAMPLE 2

The addition of different concentrations of biocide to bioluminescent E. Coli RMT1/pBL399 affects the biolumi- nescence in a dose responsive way. This experiment aims to demonstrate that the dose responsive effect is retained, even when the organisms are irradiated.

Materials
RMT1/pBL399 LUX biocide assay light reagent batch A (unirradiated) and batch B (irradiated).
BAR4 buffer (25 mM HEPES, pH 6, 75 mM NaCl, 12.5 mM $MgSO_4$).
Luminometer
Sarstedt calibration vials.
Bronopol Aldrich 13,470–8.
Analar water BDH.

Method
1. 600 vials of the lux biocide light reagent were packed into metal tins in four upright layers. An amber dosimeter was placed into the center of each layer to record the radiation dose received.
2. The tins were exposed to gamma radiation from a cobalt-60 source, until a target dose of 8 KGy had been received.
3. 5% of the vials were selected randomly from each tin for viability testing.
4. 0 .5 ml of controlled log phase broth (CLPB [LabM, LAB152]) was aseptically injected into each of the vials selected in (3), through the rubber stopper, using a fresh sterile needle for each vial.
5. The vials were inverted to ensure that all of the contents were washed into the CLPB and incubated at 30° C. for 18 hours.
6. After incubation the entire contents of each vial was placed onto a nutrient agar plate and incubated at 37° C. for 18 hours.
7. Each plate was checked for bacterial colonies, which would indicate survival of the radiation treatment.
8. The following concentrations of bronopol were made: 2, 5, 10, 15 and 20 $\mu$g/ml.
9. 15 vials of each batch of light reagent were reconstituted using 0.5 ml BAR4 buffer and left for 10 minutes for the light to stabilise.
10. After 10 minutes the light was read and immediately 0.5 ml of biocide was added with each concentration being tested in triplicate.
11. After a biocide contact time of 2.5 minutes the light was again read.
12. The d-values were calculated and plotted on a log log graph against concentration of bronopol.

Results
The radiation dose received ranged from 7.22 KGy to 8.12 KGy, and no viable cells could be recovered from any one of the vials tested, indicating that the radiation dose had killed all of the bacterial cells in the vials.

See FIG. 2 for the results.

Line equations:

unirradiated: $\log (y) = -0.386 \log (x) + 0.605$ irradiated: $\log (y) = -0.350 \log (x) + 0.602$ Both live and dead (irradiated) RMT1/pBL399 respond to bronopol in the same dose responsive way.

EXAMPLE 3

Method
1. Vials of freeze dried luminescent bacteria were irradiated at 8 kGy as in Example 1.
2. All vials of bacteria (irradiated and non-irradiated) were reconstituted with 0.5 ml of CLPB. The non-irradiated reagent was pooled as was the irradiated.
3. 100 $\mu$l aliquots of irradiated and non-irradiated reagent were dispensed into 2×8 microtitre wells.
4. 100 $\mu$l aliquots of 40 ng/ml inducer was then added to half the wells of each type of reagent, and 100 $\mu$l of CLPB added to the remaining wells as a control. The inducer was N-($\beta$-ketocaproyl)-L-homoserine lactone, a compound known to act as an autoinducer regulating expression of LUX genes.
5. The tray was incubated at 22° C. and the light signals measured at 15 minute time intervals, and left at 22° C. overnight to be read the following morning.

The results are given in FIG. 3. These show that it is possible to induce irradiated (nonviable) non-induced biolu- minescent E. coli to react metabolically to inducer and to thence produce light.

We claim:

1. An assay reagent comprising bacterial cells which have been killed but which retain a functional metabolic activity, the reagent not containing corresponding bacterial cells which have not been killed.

2. An assay reagent as claimed in claim 1 wherein the functional metabolic activity is bioluminescence.

3. An assay reagent as claimed in claim 1 or claim 2, wherein the cells have been killed by radiation.

4. An assay reagent as claimed in claim 3, wherein the functional metabolic activity is altered in a dose-responsive way by a chemical compound which alters the functional metabolic activity in a dose-responsive way in the corresponding non-irradiated cells.

5. An assay reagent as claimed in claim 1, wherein the cells are genetically modified.

6. Lyophilized bacterial cells which have been killed but which retain a functional metabolic activity.

7. A method of assaying an analyte, by the use of an assay reagent comprising a liquid suspension of signal-generating cells, which comprises mixing together a liquid sample suspected of containing the analyte and an aliquot of the assay reagent to form a test mixture, and thereafter observing a signal generated by the cells, wherein the assay reagent comprises bacterial cells which have been killed but which retain a functional metabolic activity, the reagent not containing corresponding bacterial cells which have not been killed, and wherein the functional metabolic activity of the cells is signal-generating.

8. A method as claimed in claim 7, wherein the analyte is an inducer of gene expression in the killed cells.

9. A kit for performing an assay method wherein the kit comprises: a supply of bacterial cells which have been killed but which retain a functional metabolic activity, said bacterial cells being in a lyophilized state, a supply of a reconstitution buffer; and means for handling the liquid samples and liquid aliquots.

* * * * *